United States Patent [19]
Amer et al.

[11] Patent Number: 5,275,819
[45] Date of Patent: * Jan. 4, 1994

[54] DRUG LOADED POLLEN GRAINS WITH AN OUTER COATING FOR PULSED DELIVERY

[75] Inventors: Moh. S. Amer, Carpinteria, Calif.; Rashad Tawashi, Beaconsfield, Canada

[73] Assignee: Amer Particle Technologies Inc., La Jolla, Calif.

[*] Notice: The portion of the term of this patent subsequent to May 7, 2008 has been disclaimed.

[21] Appl. No.: 691,862

[22] Filed: Apr. 26, 1991

Related U.S. Application Data

[63] Continuation-in-part of Ser. No. 306,170, Feb. 6, 1989, Pat. No. 5,013,552.

[51] Int. Cl.$^5$ ............................ A61K 37/26; A61K 9/54
[52] U.S. Cl. .................................... 424/408; 424/43; 424/45; 424/469; 424/470; 424/471; 424/472; 424/490; 514/826; 514/866; 514/964
[58] Field of Search ................ 424/408, 43, 45, 469, 424/470, 471, 472, 490; 514/826, 866, 964

[56] References Cited

U.S. PATENT DOCUMENTS

| | | | |
|---|---|---|---|
| 3,247,066 | 4/1966 | Milosovich, Jr. | 424/490 X |
| 3,922,339 | 11/1975 | Shear | 424/490 X |
| 3,937,668 | 2/1976 | Zolle | 424/490 X |
| 4,579,730 | 4/1986 | Kidron et al. | 424/490 X |
| 4,728,512 | 3/1988 | Mehta et al. | 424/458 |
| 4,933,185 | 6/1990 | Wheatley et al. | 424/461 |
| 5,011,692 | 4/1991 | Fujioka et al. | 424/426 |
| 5,013,552 | 5/1991 | Samir Amer et al. | 424/408 |

*Primary Examiner*—Paul R. Michl
*Assistant Examiner*—Robert H. Harrison
*Attorney, Agent, or Firm*—Samson B. Leavitt; Michael A. Leavitt

[57] ABSTRACT

A pulsating release composition comprising natural microspheres, such as pollen grains or spores, into which are loaded a biologically active is subsequently releasable therefrom in a predetermined location in or on a plant or animal in a series (generally 3 or more) of pulses. In one preferred embodiment, the composition comprises a group of substantially similar loaded microspheres coated with multiple barrier layers alternating with multiple active substance layers in a concentric onion-like structure, the barrier layers being slowly soluble to delay release of active substance from the underlying layer thereof until after the pulse of active substance provided by the overlying layer has subsided. In another preferred embodiment, the composition comprises a plurality of loaded microspheres divided into as many fractions as the desired number of pulses, the loaded microspheres in each consecutive fraction being coated with a barrier layer adapted to dissolve consecutively more slowly to delay release of active substance from such fraction until after the pulse of active substance provided by the prior fraction of consecutively more soluble barrier-coated microspheres has subsided. In another aspect of the invention, the active substance-containing bodies in the compositions may be coated with one or a mixture of absorption-promoting enzymes.

17 Claims, No Drawings

DRUG LOADED POLLEN GRAINS WITH AN OUTER COATING FOR PULSED DELIVERY

RELATED APPLICATION DATA

This application is a continuation-in-art of U.S. patent application Ser. No. 07/306,170, now U.S. Pat. No. 5,013,552, which was filed on Feb. 6, 1989.

FIELD OF THE INVENTION

This invention relates to new and improved biologically active compositions or formulations in which a drug or other biologically active substance is loaded into or impregnated into the interstices or pores of a natural microsphere, such as a pollen grain or a spore and/or suitably coated thereon and then released therefrom in a pulsating fashion at the target sites in or on a plant or animal (including humans).

BACKGROUND OF THE INVENTION

Historically, many methods have been developed to improve the delivery of drugs to their target organs and to allow drug release over prolonged periods of time. These controlled drug release methods generally involved the use of carrier systems to carry the drug to the vicinity of its target organ (usually the blood stream) where it released on initial dose of the drug as rapidly as possible to achieve the desired therapeutic level and then provided for a further sustained release of the drug at a desired substantially constant rate to maintain the same therapeutic level of the drug during the predetermined period of activity.

Our prior co-pending application Ser. No. 07/306,170, now U.S. Pat. No. 5,013,552 which is incorporated herein by reference discloses a composition of matter comprising a plant pollen grain, the pores or interstices of which are loaded (impregnated) with a biologically active substance, which loaded substance is releasable in or on a plant or an animal and is foreign to a naturally occurring pollen grain. That invention was, in part, based on our discovery that pollen grains could be modified by removing their natural contents and substituting or loading therein a variety of biologically active materials, such as drugs, chemicals and other pharmacologically active substances, which could then be delivered to target organs, fluids, sites, surfaces or areas in or on plants and animals, where the substance contained within the pollen grains would be released in a manner akin to the normal release of the natural contents of pollen grains in the pollination process. The use of loaded pollen grains as delivery vehicles was found to be particularly useful in the transfer of molecules, and especially large macromolecules, into the blood stream, since they usually cannot otherwise be absorbed therein or reach the circulatory system. Since the rugged or spiny surface of each pollen grain adheres to tissue surfaces and particularly to mucous membranes, the loaded pollen grains disclosed in said prior application were assured of remaining in contact with the target organ for prolonged periods of time during which the active substance was released in situ. However, no other provision was made to prolong or otherwise control the release of the loaded substance contained therein. It has also been found that spores may be utilized in the same fashion as plant pollen grains.

A number of investigators have observed, though, that the effects of certain hormones, including insulin and native ganodotropin releasing hormone (GNRH), are a function of the rate of change in their serum level rather than in their absolute level. Sensitive assay techniques, such as radioimmunoassay, now show that many natural hormones are released in pulses rather than at a steady rate. It has been found that such pulses occur about every 12-15 minutes for insulin and about every 6 minutes for GNRH. These observations may explain why in cell-free preparations, the initial response to a particular hormone disappears in the continued presence of the stimulating hormone. In in vitro experiments, if the supernatant liquid still containing the hormone to which no response is being elicited is added to a naive preparation (one not previously exposed to the hormone), a response to the supernatant liquid is again observed. This suggests that the hormone is still active and that the rate of change in its concentration may be more important in eliciting a response than its absolute level in the surrounding medium.

OBJECTS OF THE INVENTION

It is, accordingly, an object of this invention to provide a composition, delivery system or vehicle adapted or effective to release one or a mixture of biologically active substances in or on a plant or animal in pre-determined, cyclic, pulsatile or intermittent timed release manner, i.e. with peaks and valleys.

It is another object of this invention to provide a delivery system capable of releasing biologically active substances in a pulsating manner to target sites in or on plants or animals.

Another object of this invention is to further provide such a delivery system with surface or contact means adapted to or effective to improve, expedite or increase the transfer and/or absorption of the biologically active substance to or in such target sites.

A further object of this invention is the provision of methods for preparing and administering such delivery systems.

Other objects and features of this invention will be apparent from the following description.

SUMMARY OF THE INVENTION

The attainment of one or more of such objects is made possible by this invention which, in accordance with certain of its aspects, is directed to a pulsating release composition comprising an assemblage, collection or plurality of natural microspheres internally loaded with, in substitution for natural contents thereof, a biologically active substance different from such natural contents and pulsatingly releasable from the loaded microspheres by means of one or more relatively insoluble barrier layers thereon adapted to delay release of the underlying body of active substance until after the pulse provided by the previously released active substance has subsided.

Otherwise stated, the invention comprises a pulsating release composition, system, formulation, article or device comprising a plurality, series, or collection of porous or hollow natural microspheres such as pollen grains and spores from which natural contents have been removed and into which are loaded or impregnated a biologically active substance which is adapted to be released in predetermined or controlled amounts, rates, frequencies and locations in or on a plant or animal in pulsatile manner by means of one or more relatively insoluble barrier layers adapted to delay release of the underlying body of active substance until after the pulse provided by the previously released active substance has subsided.

It is only when a first pulse of active substance is released, reaches the desired therapeutic or other biological activity, peak, amplitude or level, in the target site, fluid, mucous, blood or plant serum, and dissipates, subsides, diminishes or terminates is a second pulse of active substance released. Similarly, after the second pulse reaches its desired peak or level which may be higher, lower but usually substantially the same as the previous peak, and similarly drops or dissipates, is a third pulse of active substance released and so on for as many pulses as have been provided in the formulation, composition, or assemblage.

DETAILED DESCRIPTION OF THE INVENTION

The pulsatile delivery of biologically active substances according to the invention can be accomplished in several ways. Common to all such ways, a plurality, assemblage, series, group, or collection (hereafter "assemblage") of natural microspheres, e.g. pollen grains, spores, etc., are treated to remove most or all of their natural contents and the resulting evacuated, empty, hollow porous microspheres are then loaded (impregnated) with the biologically active substance (which may be one or a mixture of biologically active substances), in partial or complete substitution for the original, natural contents which have been removed as substantially described in our said prior application, which description is incorporated here.

Then, according to one preferred aspect or embodiment of the invention (hereafter "Class I") the assemblage of loaded microspheres is divided into as many fractions as the desired number of pulses and the individual microspheres in each consecutive fraction coated with a barrier layer of sufficient predetermined consecutively increasing insolubility (resistance to dissolution) in the target animal or plant mucous, or fluid to provide the desired consecutive pulse release of active substance after the pulse provided by the prior fraction of consecutively less insoluble (more soluble) barrier layer-coated micropheres has subsided.

The Class I pulsating release system thus comprises an assemblage of fractions or groups or series of natural microspheres loaded with a biologically active substance different from the original contents of the microspheres, the microspheres in the fraction adapted to provide each successive or consecutive pulse of said substance bearing a barrier layer sufficiently more insoluble than the barrier layer carried by microspheres in the fraction providing the prior pulse to delay release (by delayed solvation of degradation of the barrier layer) of the succeeding pulse until the prior pulse has subsided, the number of fractions corresponding to the number of pulses of said substance delivered by the system.

Otherwise stated, the Class I pulsating release composition comprises a series of fractions each containing a plurality of natural microspheres each loaded with a biologically active substance different from the natural contents of the microspheres and coated with a relatively insoluble carrier layer, the barrier layers in any fraction being sufficiently more insoluble than those in the prior fraction to delay release of a pulse of said substance from the microspheres in said any fraction until after the pulse released from the microspheres in said prior fraction has subsided, the number of pulses released by the composition substantially corresponding to the number of fractions therein. The first fraction, i.e. the fraction which releases the first pulse, contains microspheres loaded with the active substance and which may but usually does not carry a barrier layer.

According to a second preferred embodiment or aspect of the invention (hereafter "Class II"), the composition comprises an assemblage of natural microspheres similarly loaded with a biologically active substance, each carrying substantially similar multiple relatively insoluble barrier layers alternating with multiple layers of biologically active substance in an onion-like multilayered structure, each active substance layer being adapted to rapidly release said substance at the target site and/or in animal or plant fluid to provide the desired pulse activity, each barrier layer being sufficiently insoluble in animal or plant fluid to delay release of said substance (by delayed solvation or degradation of the barrier layer) from the underlying active substance layer until after the pulse of said substance provided by the overlying active substance layer has subsided, the number of active substance layers corresponding roughly to one less than the desired number of active substance pulses. In this Class II type system, the first pulse of active substance is provided by the combined simultaneous release of the substance from the outermost active substance layers on all the loaded microspheres, and the final pulse is provided by the combined simultaneous release of the active substance from within the loaded microspheres.

The several values, parameters or functional properties desirable for carrying out the present invention are readily predetermined by routine experimentation. The peak activity, amplitude or concentration desired to be reached in each pulse will of course vary with the drug or other biologically active substance being administered, for any particular active substance, the peak activity and the elapsed time from initial release thereof from the active substance layer or from the pores or interior of the microsphere until the peak activity is reached and then subsides to its bottom or valley activity will depend on the dispersibility or solubility of the active substance in the fluid at the target site and the amount of such substance in the layer or microsphere. Typically the elapsed time from release to peak may range from about one to about one hundred minutes, and from peak to minimum, bottom or valley activity from about five minutes to about one hour or more to permit the active substance to complete its intended function. The minimum valley activity typically ranges from a theoretical zero to less than about fifty percent of the peak activity (concentration) and may be extended in duration until the activity begins to rise by release of the next pulse—providing charge of biologically active substance.

In the Class II system, depending on the solubility (or insolubility, resistance to dissolution, dispersion, degradation or disintegration) of each barrier layer, its thickness is adjusted so that its dissolution or degradation in the said fluid, beginning when the overlying layer of active substance has been released, dispersed, or dissolved, is sufficiently completed at or after the time when the activity of said released active substance has subsided to or adjacent to its bottom or valley activity to enable initiation of release of active substance from the underlying active substance layer or from the microsphere itself.

In the Class I system, the first pulse of biologically active substance is released by the first fraction containing the loaded usually uncoated microspheres. The second pulse is released by the second fraction containing loaded microspheres each coated with a barrier layer predetermined to dissolve or disintegrate at a sufficiently low rate to delay release of the pulse of active substance from the base loaded microspheres in the second fraction until after the pulse released by the first fraction has subsided. The third pulse is released by the third fraction containing loaded microspheres, each coated with a barrier layer predetermined to dissolve or disintegrate at a sufficiently lower rate (by use of a thicker coat of the same film forming material and/or a coat or layer of a more insoluble material) to delay release of the pulse of active substance from the base loaded microspheres in the third fraction until after the pulse released by the second fraction has subsided. And so on for as many pulses (and corresponding fractions) as desired.

The barrier layers in both the Class I and Class II systems described above are typically formed from or have a base of a film-forming bio-compatible and drug- (or other biologically active substance) compatible material. A "bio-compatible" material is compatible with the environment in which the systems of this invention are introduced and function, i.e. is non-toxic and inert (non-reactive, non-degradive, etc.) to the contacted animal and plant fluid and other parts, in addition of course to having the desired above-described controlled or delayed solubility in the fluid. A "drug-compatible" (or "active substance compatible") material is compatible with the biologically active substance being employed, i.e., is inert to (non-reactive with, insoluble in, and incapable of solubilizing or dissolving) such active substance, being thus dependent on the particular active substance being formulated and the intended end use in plant or animal or part thereof. The film-forming material may accordingly be any suitable type, natural or synthetic, organic or inorganic, thermoplastic or thermosetting, and having or being adapted to be formulated to have a predetermined degree and rate of solubility (disintegration, degradation, etc.) in the plant or animal part or fluid with which it will contact during use.

The barrier layer may preferably be composed substantially entirely of film-forming material or of a formulation of such material with plasticizers, extenders, fillers, and other common excipients predetermined to provide or deposit a layer with the desired rate of solubility or degradation in the plant or animal fluid. By "film-forming" is meant the property of forming a solid film, coating or layer at ambient or room temperatures. If the film-forming material is thermoplastic or capable of being melted or liquified at elevated temperatures, it may be applied to the microsphere or underlying layer of active substance by spray, immersion, or other means of deposition in heated liquified form and cooled in situ, which, however, is ordinarily not preferred in view of possible detrimental action on the underlying biologically active substance. Preferably, the barrier layer is formed by deposition of a solution or dispersion of the film-forming material at cool or ambient temperatures in an aqueous or an inert non-toxic volatile organic solvent followed by drying the deposited film in situ.

The materials employed in these barrier layers, and their methods of preparation and application to the underlying microsphere or biologically active substance-containing layer are well known in the microencapsulation and drug controlled release art and are, for example, described in the Kirk-Othmer Encyclopedia of Chem. Technology, 3rd Ed. 1981, John Wiley & Sons, Vol. 15 "Microencapsulation", pp 470–493 and Vol. 17 Pharmaceuticals, Controlled Release, pp 290–310, which descriptions are incorporated here. As supplemental examples of suitable film-forming materials there may be mentioned, when the active substance would be deleteriously affected by the stomach gastric acids (pH about 1–3), enteric coatings which resist such breakdown and are dissolved by intestinal fluids (pH about 5.5–10) such as polyvinyl methylether/maleic anhydride copolymer (PVM/MA), shellac, a composition containing 40–50, preferably 45, parts of a fatty acid ester such as n-butylstearate, 15–25, preferably 20, parts of a wax such as carnauba wax, 20–30, preferably 25, parts of a fatty acid such as stearic acid, and 5–15, preferably 10, parts of a cellulose ester such as cellulose acetate phthalate, deposited from a solution in about 400–900 parts of inert non-toxic solvent such as alcohol and/or acetone, etc. Other types of coatings or barrier layers suitable for oral ingestion, inhalation, skin treatment or systemic administration as by intramuscular, intraperitoneal, or intravenous injection may be employed.

Other examples of suitable film-forming barrier materials include polymethylsiloxane, polyacrylamide, polyvinyl pyrrolidone (PVP), polyvinyl alcohol, ethylene/-vinyl acetate copolymer, polyesters, polyurethanes, polycarbonates, polystyrene, polymethyl methacrylate, polyvinyl acetate, polyols, polythiols, polyamines, polyethylene, polypropylene, cellulosics such as regenerated cellulose, ethyl cellulose, cellulose acetate butyrate (CAB), fats, waxes, etc. Synthetic polymeric materials are preferred.

The natural microspheres of the present invention comprise unique pulsatile carriers of active materials, including drugs, when compared to pellets, granules, beads, or conventional microspheres because they resist degradation, have unique size and shape and characteristics providing excellent bioadhesion and therefore longer retention time, and may, as described below, be covered with enzymes (as in their natural state) to provide fast transfer, permeation and absorption.

A variety of pharmaceutical preparations according to the invention may be formulated. These preparations are suitable for oral, topical, or parenteral administration, including tablets, capsules, powders, capulets, lozengers, aerosols, suppositories, external creams and ointments, and liquid dispersions, suspensions or solutions for injection.

Moreover, in accordance with a further aspect of the invention, the above described active substance-carrying microspheres may be coated with one or a mixture of enzymes that are adapted and function to facilitate the transmucosal absorption of the active substance contained therein. The mechanism by which such facilitation occurs is not understood, but it is theorized that the enzymes upon contact with a moist surface render such surface, by chemical and/or physical mechanism, susceptible to penetration by the active substance. Thus, when the loaded pollen grains of this invention are coated with the same enzymes that coat the naturally occurring pollen grain, these enzyme-coated loaded natural microspheres reproduce what occurs in nature. Accordingly, the enzymes employed will vary from one pollen grain species to another, as occurs naturally, but, in general, these enzymes include, but are not limited to, oxidoreductases, transferases, hydrolases, ligases, lyases, peroxidases, estrases, phosphatases, peptidases and mixtures thereof. Such enzymes are commercially available from several biochemical supply companies, including Sigma, Wako and Fisher.

In common with the loaded pollen grain system described and claimed in our corresponding application Ser. No. 07/306,510, the pulsating release system of this invention provides or enables:

i) Bioadhesion of the pollen grain based natural microsphere drug carriers taking place on the mucosa (e.g. oropharynx or the upper lung):

ii) Adhesion due to the characteristics of the mucosal surface and the surface geometry of the selected pollen grains;

iii) Bioavailability of the active ingredient (e.g. drug) due to the uniformity of the particle shape and the very narrow size distribution of the pollen grains thereby allowing for accurate control of the dose of active ingredient loaded therein and released;

iv) Drug release based on the impermeability of the surface coat and the release characteristics imposed by the limited number of pores of predetermined dimension.

Thus, using pollen grains, with their distinctive surface geometry and uniform size, as drug carriers can improve bioadhesion to the mucosal surface allowing for better, longer, and closer contact with the absorptive surface, resulting in a more efficient drug delivery system. Moreover, the uniform size of the pollen grains, their impermeable surfaces and the predetermined and limited area of contact of the loaded drug with the surrounding medium increase the predictability of the release process and facilitate accurate control of the rate of drug release and absorption.

ILLUSTRATION OF THE DELIVERY SYSTEM

1) The Pollen Deproteination

Ragweed pollens are deproteinated by adding 2 grams of dried pollen to 10 ml of 6N Hydrochloric acid (HCl) and heating in a hot air oven, in closed strong glass tubes for 24 hours at 110° C.

The pollens are separated by filtration, washed with distilled water until free from acidity, dried under vacuum, and kept for further processing.

2) The Pollen Carrier Loading

Peptides, such as insulin and angiotensin, are loaded (impregnated) into the pollen carrier by using one part by weight of the peptide to two parts by weight of deproteinated vacuum dried pollens to provide a concentration of 2–25%. Release of insulin and angiotensin from the pollen grains is established by measurement in vitro. It should also be understood that while the active ingredients are loaded into the natural microspheres (pollen grains or spores), it may occur that some of the actives may remain on their outer surfaces.

A. Insulin Loading in Pollen 200 mg of bovine insulin is dissolved in 1 ml of N/10 HCl, then neutralized to pH 7.4 by N/10 NaOH. 5 ml of 4% sodium deoxycholate solution (providing 200 mg of deoxycholate) is added. 400 mg of deproteinated vacuum dried pollens are added to the insulin solution in deoxycholate. The suspension is left under vacuum at 0° C. for 24 hours.

The suspension is shaken in a Turbula mixer at 4° C. for 24 hours. The suspension is then dried by vacuum centrifugation at 0° C. The final concentration of insulin is 25% weight per weight (25 unit/4 mg carrier) (6 units/1 mg carrier). 1 mg of insulin equals 25 units.

B. Angiotensin Loading in Pollen 5 mg of the peptide angiotensin is dissolved in 1 ml of distilled water by sonification in an ice bath. To this solution, 40 mg of dried deproteinated pollens are added. The suspension was mixed in a Turbula mixer for 24 hours at 0° C. The final concentration of angiotensin is 10% weight per weight.

3) Illustrative Procedure Used for the Preparation of Class I type Peptide Loaded Pollens With Different Release Characteristics for Buccal Tablets, Aerosols, and Suppositories Using Polymer Film Coating Different fractions of peptide, (e.g., insulin) loaded pollens may be prepared to give repeated or pulse action in the following ways:

i. The first fraction consists of a group of pollens or spores containing active peptide which provides the first pulse.

ii. The second fraction consists of a similarly loaded group coated with a relatively fast-dissolving barrier film of hydroxypropylcellulose (HPC)* which thus provides the second pulse by releasing the peptide active from the loaded pollens after the first pulse has subsided.

iii. The third fraction consists of a similarly loaded group coated with as lower dissolving barrier film of hydroxypropyl methyl cellulose (HPMC)** (2–4 microns thick), thus providing the third pulse by release of the loaded peptide after the second pulse has subsided.

iv. The fourth fraction consists of a similarly loaded group coated with a still slower-dissolving barrier film of cationic copolymer based on methacrylic acid and dimethyl aminoethyl methacrylate (DMAEM)*** resin film (3 microns thick), thus providing the fourth pulse.

v. The fifth fraction consists of a similar group coated with a still slower-dissolving barrier film of the same cationic copolymer (5 microns thick), thus providing the fifth pulse.

*A polymer soluble in (cold) water, lower alcohols, and gastrointestinal fluids, available as Klucel ® from Hercules.

**A polymer soluble in water, methylene chloride, and gastrointestinal fluids, available as Methocel HG ® from Dow Chemical.

***A copolymer soluble in organic solvents such as isopropanol, available as Eudragit ® R. L. from Rhom Pharma GmbH of Germany. It provides a smooth, uniform delayed action film, and it may be used with HPMC in combination to produce other fractions of the pulsatile release loaded microspheres of the present invention.

All coated and non-coated fractions are treated with an enzyme (e.g. transferase) acting as an active substance delivery enhancer. These enzymes are used to coat each fraction separately.

4) Class I Coating Procedures

The following coating procedure is applicable to the multiple dose units used to prepare buccal tablets, suppositories, and metered dose inhalers (aerosols).

Different thicknesses of polymer films on loaded micropheres in the different fractions are obtained by suspending the peptides (e.g. angiotensin) loaded pollens in isopropanol of methylene chloride solutions of successively increasing concentrations of the polymer. Suitable polymers include HPC, HPMC and DMAEM copolymer. The concentration of polymer will control the film thickness, which will vary between 2-5 micrometers and will be determined by image analysis technique from boundary movement of the original microspheres (pollen). Film coating will be carried out at room temperature, and solvent evaporation will be carried out by vacuum centrifugation at 0° C. to prevent degradation of the peptides.

Each fraction (a group of peptide-loaded, barrier-coated pollens) mentioned above, or only the uncoated peptide-loaded pollens, may be further coated with one or a mixture of enzymes enhancing absorption, to facilitate transmucosal absorption. The enzymes are applied to the individual fractions or uncoated peptide loaded pollens from an aqueous alcohol solution using a spray at 4° C. followed by drying at 4° C. under vacuum.

A desired pulse release sequence may be obtained by appropriate blends of the fractions described above, taking into consideration the release characteristics of each fraction, their absorption and elimination rate constant, and the therapeutic level of the peptide action.

5) Illustrative Class I Type Pulse Release

The following table illustrates the time factors involved in the pulse release of peptide, e.g. insulin, angiotensin, from 50% peptide-loaded pollen grains in 5 fractions, uncoated and coated with 5%, 10%, 15% and 20% HPMC similar to preceding Illustrations 3) and 4).

| | Peptide Release Time in Minutes | | | | |
|---|---|---|---|---|---|
| | Uncoated | 5% Ctd | 10% Ctd | 15% Ctd | 20% Ctd |
| 50% Insulin | 7.5 | 15 | 30 | 45 | 90 |
| 50% Angiotensin | 15 | 30 | 45 | 60 | 90 |

6) Release Characteristics—Pulse vs. Sustained Release

The following table represents the theoretical expectation from a pulsatile release formulation vs. a sustained release formulation:

| Time (min) following | Blood Concentration (μU/ml) | |
|---|---|---|
| Administration | Sustained Release | Pulse Release |
| 0 | 0 | 0-10 |
| 5 | 20-30 | 20-30 |
| 15 | 40-50 | 40-50 |
| 30 | 40-50 | 0-10 |
| 45 | 40-50 | 20-30 |
| 60 | 40-50 | 40-50 |
| 75 | 40-50 | 0-10 |
| 90 | 40-50 | 20-30 |
| 105 | 40-50 | 40-50 |
| 120 | 40-50 | 0-10 |
| 135 | 40-50 | 20-30 |
| 150 | 40-50 | 40-50 |
| 165 | 40-50 | 0 |
| 180 | 40-50 | 20-30 |
| 195 | 40-50 | 40-50 |

The term "biologically active substances" as employed herein and in the appended claims has a well known, science recognized meaning and includes a wide variety of biologically active substances, as illustrated below, which may be loaded into the pollen grains of this invention for subsequent pulsatile release. They comprise simple and complex chemicals, drugs, and other pharmacologically active substances. Said term is disclosed, defined and/or illustrated in, for example, U.S. Pat. Nos. 4,898,824, 4,900,556, 4,906,570 and 4,921,757 which disclosures, definitions and illustrations are applicable and herewith incorporated herein.

Examples of drugs include:

Anaesthetics, local: Xylocaine, eugenol, etc.
Analgesics: Ibuprofen, etc.
Anti-acne: Retenoic Acid.
Antibacterials
Antibiotics: Neomycin, tetracycline, etc.
Anti-cariogenic drugs: Fluorides (for use in toothpastes), etc.
Anti-inflammatory drugs: Cortisone acetate, prednisolone, etc.
Anti-viral agents
Aromatics: Cinnamon, clove oil, etc.
Biocides
Cytotoxics (for local anti-tumor therapy): Mitomycin, etc.
Flavoring agents: Menthol (in toothpaste), etc.
Fragrances
Hormones
Proteins and peptides: Insulin, calcitonin, angiotensin, etc.
Steroids Examples of biologically active substances for plant treatment include:

Herbicides: 2,4-D; 2,4,5-T; TCDD; alachlor; amiben; barban; diuron; paraquat; propanil; propham; etc.
Hormones; Pheromones
Insecticides: Benzyl benzoate, organophosphorous compounds, carbamates, pyrethrins, etc.
Larvicides: Synthetic perthroids, etc.
Nematocides
Pesticides: DDT, aldrin, benzene hexachloride, chlordane, dieldrin, heptachlor, methyl bromide, phosphine, rotenone, etc.
Plant Growth Regulators The pollen grains in pulsatile release form according to this invention can be incorporated into any type of pharmaceutical formulation or dosage form for administration to humans or animals, including aerosols, buccal and sublingual tablets, oral tablets, multilayered tablets, capsules, caplets, surgical implants, lozenges, nasal sprays, creams and ointments, injectables, parenterals, transdermal patches, liquids, mouthwashes, nose drops, dental floss, and the like. They can also be enteric coated.

They can also be used to introduce substances into or on plants by a pollination-like system.

The following examples illustrate the best modes contemplated for carrying out this invention. All amounts and proportions are by weight and temperatures are in °C. as referred to herein and the appended claims unless otherwise indicated.

EXAMPLE I

Class 1 (5 Pulses)

Buccal tablets having a disintegration time of 20 seconds may be comprised of the following ingredients:

| Free Peptide (Crystalline Insulin) | |
|---|---|
| Initial Pulse Dose | 5-10 units |
| Blend of four different fractions of coated and one fraction of uncoated insulin loaded pollen grains (or spores), enzyme coated* | 5-10 units/ea fraction |

-continued

| Free Peptide (Crystalline Insulin) | | |
|---|---|---|
| Cabosil (Fumed Silica) | | 1 mg. |
| Magnesium stearate | | 2 mg. |
| Mannitol Crystalline (N.F.) | Q.S. | to 100 mg. |

The tablet is prepared by mixing of the ingredients and by direct compression of the mixture into 100 mg. tablets.

*The above blend contains the following mixture of fractions:
1) Free crystalline insulin-loaded pollen grains (enzyme coated) that will be released immediately and over a 5 minute period.
2) Insulin loaded in natural microspheres (pollen grains) and coated with hydroxypropyl cellulose (HPC) that will release insulin in 15 minutes and over a 5 minute period.
3) Insulin loaded in natural microspheres (pollen grains) and coated with hydroxypropyl methyl cellulose (HPMC) that will release insulin in 30 minutes and over a 5 minute period.
4) Insulin loaded in natural microspheres (pollen grains) and coated with cationic copolymer based on methacrylic acid and DMAEM that will release insulin in 45 minutes and over a 5 minute period.
5) Insulin loaded in natural microspheres (pollen grains) and covered with a thicker coat of the same cationic copolymer used in 4) above that will release insulin in 60 minutes and over a 5 minute period.

The pollen grains are coated with one or a mixture of enzymes such as oxidoreductase, transferase, etc. as previously discussed, to facilitate the transmucosal absorption of the released insulin.

In the case of such class I multiple dose units, the polymer film thickness ranges between 3 and 5 micrometers. The loaded pollen grains are mixed with the appropriate amount of the polymer solution in organic solvent at 4° C. and dried by vacuum centrifugation at 0° C.

EXAMPLE ii

Class II multilayer Concentric Tablets

A concentric buccal tablet (onion like) is prepared containing layers of crystalline insulin alternating with barrier layers, films or coats of hydroxypropylcellulose (HPC) or a mixture of HPC and HPMC or a similar coating with predetermined dissolution characteristics. In use after each barrier coat is dissolved, a fresh layer of insulin is exposed and another pulse of insulin is released. Such a tablet can be prepared containing as many insulin layers as the needed pulses. The outermost layer preferably contains free crystalline insulin separated from a second (underlying) insulin layer by the barrier polymer coat. The second insulin layer is separated from a third insulin layer by another polymer coat and so on. After the release and absorption of the outer most insulin layer, the first polymer coat delays the release and absorption of the second insulin layer. As each polymer film or coat disintegrates, a new insulin pulse is released. This can go on for as many pulses as desired. These onion-like insulin tablets may be prepared by initial direct compression of the central core consisting of the insulin-loaded pollen grains which provide the final pulse. This core is then coated first with a polymer barrier layer and then successively with insulin layers alternating with 20 microns thick layers of polymer barrier layers for as many pulses (minus one) as desired. The polymer layers may be applied to the central core and the underlying insulin layers as, for example, described above in a coating pan by spray gun followed by drying in cold air at 4° C. using as polymer solution a 1:1 DMAEM/methacrylic acid copolymer in isopropanol or HPMC in toluene (10% concentration). The insulin layers may be similarly applied to the underlying polymer barrier layers as by spraying the barrier coated pollen grains in a coating pan with a solution of the desired concentration of insulation in deoxycholate, prepared as described above under "A. Insulin Loading in Pollen," followed by drying in cold air at 0° C. The outermost layer may be a polymer barrier coat or preferably an insulin layer (to provide the initial pulse) which may be coated with enzyme (e.g. estrase) as by spraying an alcoholic solution of the enzyme followed by drying in cold air at 4° C. to facilitate transmucosal absorption of the released insulin.

EXAMPLE III

An example of a novel five pulse oral inhalation aerosol preparation (in a metered dose inhaler) is comprised of the following components:

| Insulin loaded pollen grains | |
|---|---|
| (4 fractions coated and 1 uncoated)* | 840 mg. |
| Freon 11 | 2.3 g. |
| Freon 12 | 6.9 g. |

Each dose is 0.1 ml and is prepared by pressure filling.

*The fractions comprise the following:

| Drug Carrier Fractions | Concentration of Insulin | Coating Material | Pulse Release Initiation |
|---|---|---|---|
| 1 | 6 units/mg pollen | none | 0 min |
| 2 | 6 units/mg pollen | HPC (3 μm) | 15 min |
| 3 | 6 units/mg pollen | HPC (5 μm) | 30 min |
| 4 | 6 units/mg pollen | DMAEM (3 μm) | 45 min |
| 5 | 6 units/mg pollen | DMAEM (5 μm) | 60 min |

Freon 11 propellant is used as a dispersing agent, and Freon 12 is used as the driving force in dispensing the medication from the can in spray form. The aerosol may contain, and/or the insulin loaded (coated) pollens may be coated with, one or a mixture of enzymes as described above to facilitate transmucosal absorption of the released insulin.

The types of pollen grains that may be used in practising the invention is unlimited. However, a particularly preferred pollen grain is the Green Ash pollen grain to which no allergenic reactions are believed to have been reported. Their aerodynamic diameter is about 24–26 microns. Aerodynamic diameter is the diameter of a particle as determined from its sedimentation velocity in air. The term "diameter" may now be used, though, as it may be measured directly using image analysis, thereby eliminating the need for aerodynamic analysis.

EXAMPLE IV

An example of a novel Class I type pulse suppository, which may be used for the rectal delivery of certain peptides or proteins including insulin, vasopressin, calcitonin, gastrin, GNRH (native gonadotrophin releasing hormone) and/or decapeptide Nafarelin (which has 200 times the activity of GNRH), is comprised of the following components:

| Pollen loaded with a peptide (one fraction) | | 4 mg. |
|---|---|---|
| 4 fractions of the above coated with polymers of increasing thickness and/or insolubility as in Examples I and III | | 20 mg. |
| Tween 61 ® * | qs | 2 Gm |

(*Polyethylene sorbitan monostearate used as a water soluble base having a melting range of 35–49° C., which may be used alone or in combination with fatty or emulsified bases.)

The suppositories may be made of conventional cold molding extrusion techniques to avoid possible degradation of heat sensitive peptides.

EXAMPLE V

A novel formulation which may be used for the pulsatile release of pheromones in the form of an aerosol to disrupt the mating of codling moths in apples is comprised of the following components:

| | |
|---|---|
| 5 fractions of pollen grains loaded with pheromones uncoated and coated with Eudragit ® R.L. copolymer barrier films of suitably increased thickness for successive release characteristics from fraction to fraction | 1 gm. |
| Freon 12 | 100 gms. |

Such an insecticidal formulation could be used indoors or outdoors to provide pulsatile release, which would have certain advantages over conventional insecticides, including sustained release ones. Examples of insecticides which may be released in pulsatile form include organophosphates, carbamates, pyrethrums, and synthetic perthroids. Herbicides may also be utilized in a pulsatile release form.

EXAMPLE VI

The following data illustrates peak and valley levels of blood plasma insulin and the time intervals therebetween in a clinical human application of a 25 units dose of insulin in a three pulse oral inhalation aerosol prepared as described in EXAMPLE III.

| | Milliunits/l. blood | Time After Initiation (Hrs) |
|---|---|---|
| 1st Peak Pulse | 300 | 1.5 |
| 1st Min. Valley | 30 | 2.0 |
| 2d Peak Pulse | 600 | 3.0 |
| 2d Min. Valley | 30 | 3.5 |
| 3rd Peak Pulse | 400 | 5.0 |
| 3rd Min. Valley | 50 | 7.0 |

EXAMPLE VII

The insulin-containing layers in EXAMPLE II, and the base biologically active substance-loaded pollen grains in all the EXAMPLES are treated with one or a mixture of any of the following enzymes in the indicated concentrations as encountered in the natural pollen to provide enhanced pulsatile absorption and permeation of the biologically active substance according to this invention.

| ENZYME | UNITS/GM. POLLEN |
|---|---|
| Amylase | 1–10 |
| Diastase | 1–10 |
| Saccharase | 0.5–5 |
| Pectase | 0.1–5 |
| Phosphatase | 1–10 |
| Catalase | 0.2–4 |
| Collagenase | 1–10 |
| Cozymase | 0.3–3 |
| Cytochrome Oxidase | 0.5–7 |
| Succinic Dehydrogenase | 0.2–10 |
| Pepsin | 0.1–10 |
| Trypsin | 0.1–10 |
| Hydrolase | 0.1–20 |

It will be understood the foregoing discussion, as further explained by the specific examples, only illustrates the invention and its principles. However, many modifications and variations in the details of the disclosure will occur to those skilled in the art to which this invention relates and still remain within the scope and principles of the invention. It will be understood that obvious variations and modifications thereof that may be made by those skilled in the art are intended to be included within the spirit and purview of this application and the scope of the appended claims.

What is claimed is:

1. A pulsating release composition comprising a plurality of porous natural pollen grain microspheres each loaded at least internally with a biologically active substance foreign to the naturally occurring pollen grain microspheres, such loaded microspheres being coated with one or more barrier layers of sufficient resistance to dissolution in animal or plant fluid to delay the release of the underlying body of active substance until after the pulse provided by the previously released substance has subsided.

2. The pulsating release composition of claim 1 wherein the active substance-containing bodies in the composition carry an outer coat containing one or a mixture of absorption-promoting enzymes.

3. The pulsating release composition of claim 1, wherein said biologically active substance is selected from the group consisting of anesthetics, analgesics, antibacterials, antibiotics, anti-cariogenics, anti-inflammatories, anti-viral agents, aromatics, biocides, cytotoxics, flavoring agents, hormones, proteins and peptides, steroids, herbicides, larvicides, plant growth regulators, and pesticides.

4. The composition of claim 3 wherein the biologically active substance comprises insulin or angiotensin.

5. The pulsating release composition of claim 1 embodied in a form selected from the group consisting of aerosols, buccal tablets, sublingual tablets, oral tablets, multilayered tablets, capsules, caplets, surgical implants, lozenges, nasal sprays, creams and ointments, injectables, parenterals, transdermal patches, liquids, mouthwashes, nose drops, and dental floss.

6. A pulsating release composition according to claim 1 wherein the individual internally loaded pollen grain micropheres are coated with multiple relatively insoluble barrier layers alternating with multiple layers of biologically active substance in a concentric onion-like structure, each active substance layer being adapted to rapidly release said substance in animal or plant fluid to provide the desired pulse activity, each barrier layer being sufficiently insoluble in said fluid to delay release of said substance from the underlying active substance layer until the pulse provided by the overlying substance layer has subsided.

7. The pulsating release composition of claim 6 wherein said biologically active substance is selected from the group consisting of anesthetics, analgesics, antibacterials, antibiotics, anti-cariogenics, anti-inflammatories, anti-viral agents, aromatics, biocides, cytotoxics, flavoring agents, hormones, proteins and peptides, steriods, herbicides, larvicides, plant growth regulators, and pesticides.

8. The pulsating release composition of claim 6 wherein said biologically active substance comprises insulin or angiotensin.

9. The composition of claim 6 embodied in a form selected from the group consisting of aerosols, buccal tablets, sublingual tablets, oral tablets, multilayered tablets, capsules, caplets, surgical implants, lozenges, nasal sprays, creams and ointments, injectables, parenterals, transdermal patches, liquids, mouthwashes, nose drops, and dental floss.

10. The pulsating release composition of claim 6 wherein each layer of biologically active substance is coated with at least one absorption-promoting enzyme.

11. A pulsating release composition according to claim 1 wherein the plurality of loaded pollen grain microspheres are divided into as many fractions as the desired number of pulses, the loaded pollen grain microspheres in each consecutive fraction being coated with barrier layers of sufficient predetermined consecutively increasing resistance to dissolution in animal or plant fluid to provide the desired consecutive pulse release of active substance after the pulse provided by the prior fraction of consecutively more soluble barrier layer-coated pollen grain microspheres has subsided.

12. The pulsating release composition of claim 11 wherein said biologically active substance is selected from the group consisting of anesthetics, analgesics, antibacterials, antibiotics, anti-cariogenics, anti-inflammatories, anti-viral agents, aromatics, biocides, cytotoxics, flavoring agents, hormones, proteins and peptides, steroids, herbicides, larvicides, plant growth regulators, and pesticides.

13. The pulsating release composition of claim 12 wherein said biologically active substance comprises insulin or angiotensin.

14. The pulsating release composition of claim 11 embodied in a form selected from the group consisting of aerosols, buccal tablets, sublingual tablets, oral tablets, multilayered tablets, capsules, caplets, surgical implants, lozenges, nasal sprays, creams and ointments, injectables, parenterals, transdermal patches, liquids, mouthwashes, nose drops, and dental floss.

15. The pulsating release composition of claim 11 wherein the individual loaded pollen grain microspheres are coated with at least one absorption-promoting enzyme.

16. A method of treating a plant or animal with a biologically active substance comprising administering to such plant or animal an effective amount of a composition as defined in claim 1.

17. A method of treating a plant or animal with a biologically active substance comprising administering to such plant or animal an effective amount of a composition as defined in claim 11.

* * * * *